US 12,426,819 B2

United States Patent
Shin et al.

(10) Patent No.: US 12,426,819 B2
(45) Date of Patent: Sep. 30, 2025

(54) MULTI-CHANNEL MICRO PERIPHERAL NERVE SENSOR FOR NEUROSIGNAL MEASUREMENT

(71) Applicant: KOREA ELECTRONICS TECHNOLOGY INSTITUTE, Seongnam-si (KR)

(72) Inventors: Kyusik Shin, Seoul (KR); Cheolung Cha, Seoul (KR); Yunjae Won, Seongnam-si (KR)

(73) Assignee: Korea Electronics Technology Institute, Seongnam-si (KR)

( * ) Notice: Subject to any disclaimer, the term of this patent is extended or adjusted under 35 U.S.C. 154(b) by 407 days.

(21) Appl. No.: 18/147,345

(22) Filed: Dec. 28, 2022

(65) Prior Publication Data

US 2024/0215886 A1   Jul. 4, 2024

(51) Int. Cl.
*A61B 5/24* (2021.01)

(52) U.S. Cl.
CPC .......... *A61B 5/24* (2021.01); *A61B 2562/028* (2013.01); *A61B 2562/12* (2013.01); *A61B 2562/164* (2013.01); *A61B 2562/166* (2013.01)

(58) Field of Classification Search
CPC .. A61B 5/24; A61B 2562/028; A61B 2562/12
USPC .......................................................... 607/2
See application file for complete search history.

(56) References Cited

U.S. PATENT DOCUMENTS

| | | | |
|---|---|---|---|
| 7,302,296 B1 * | 11/2007 | Hoffer | A61N 1/36021 607/46 |
| 7,783,360 B2 * | 8/2010 | Zdravkovic | A61B 5/4041 607/116 |
| 7,783,363 B2 * | 8/2010 | Zdravkovic | A61N 1/0551 607/116 |
| 8,666,499 B2 * | 3/2014 | Youn | A61N 1/36103 607/116 |
| 8,676,334 B2 * | 3/2014 | Youn | A61N 1/0551 607/48 |
| 9,220,426 B2 * | 12/2015 | Kim | A61B 5/24 |
| 10,842,611 B2 * | 11/2020 | Thian | A61F 2/0077 |
| 11,166,800 B2 * | 11/2021 | Deister | A61B 17/11 |
| 11,980,536 B2 * | 5/2024 | Deister | A61L 27/3804 |
| 11,992,319 B2 * | 5/2024 | Choi | A61N 1/0551 |
| 12,001,942 B2 * | 6/2024 | Codella | G06N 3/08 |
| 2006/0161218 A1 * | 7/2006 | Danilov | A61B 5/682 607/45 |
| 2008/0119918 A1 * | 5/2008 | Zdravkovic | A61N 1/36103 607/116 |

(Continued)

*Primary Examiner* — Shirley X Jian
(74) *Attorney, Agent, or Firm* — Knobbe, Martens, Olson & Bear, LLP

(57) ABSTRACT

A multi-channel micro peripheral nerve sensor for measuring a neurosignal with low noise is proposed. The multi-channel micro peripheral nerve sensor may include a substrate, an analog-digital (AD) converter, and a signal acquisition unit. The substrate may be combined with each cut surface of a severed nerve and include channels into which nerve cells are inserted. The AD converter may be combined with the substrate, be electrically connected to the channels, receive analog neurosignals from the nerve cells, and convert the analog neurosignals into digital signals. The signal acquisition unit may be electrically connected to the AD converter and acquire the digital signals from the AD converter.

8 Claims, 5 Drawing Sheets

(56) References Cited

U.S. PATENT DOCUMENTS

| | | | |
|---|---|---|---|
| 2008/0161867 A1* | 7/2008 | Zdravkovic | A61N 1/0551 607/2 |
| 2010/0211172 A1* | 8/2010 | Bellamkonda | A61B 5/0031 607/116 |
| 2015/0173918 A1* | 6/2015 | Herr | A61F 2/68 623/25 |
| 2015/0217109 A1* | 8/2015 | Achyuta | A61N 1/0551 607/116 |
| 2018/0296316 A1* | 10/2018 | Thian | A61F 2/08 |
| 2019/0314132 A1* | 10/2019 | Deister | A61B 17/11 |
| 2024/0164780 A1* | 5/2024 | Kehrer | A61F 2/02 |
| 2024/0215886 A1* | 7/2024 | Shin | A61B 5/4041 |

* cited by examiner

MULTI-CHANNEL MICRO PERIPHERAL NERVE SENSOR FOR NEUROSIGNAL MEASUREMENT

BACKGROUND

Technical Field

The present disclosure relates to a peripheral nerve sensor. For example, the present disclosure relates to a multi-channel micro peripheral nerve sensor that can measure a neurosignal with low noise.

Description of Related Technology

With the rapid aging of the population, the number of patients suffering from muscle paralysis due to abnormalities of the cranial nerve system, such as stroke and Parkinson's disease, continues to increase. In addition to the development of treatment by controlling the etiology, there is a need to develop rehabilitation medical technology and auxiliary medical devices for patients with muscular paralysis.

To develop effective rehabilitation medical technology, the development of neuroprosthetics technology through the convergence of medical and engineering technologies is actively underway.

SUMMARY

One aspect is a multi-channel micro peripheral nerve sensor for measuring a neurosignal with low noise and characterized by an analog-digital converter, which converts the neurosignal received from a nerve cell into a digital signal, is directly provided in a substrate combined with both ends of a severed nerve.

Another aspect is a multi-channel micro peripheral nerve sensor for measuring a neurosignal that includes a substrate combined with each cut surface of a severed nerve and including channels into which nerve cells are inserted; an analog-digital (AD) converter combined with the substrate, electrically connected to the channels, receiving analog neurosignals from the nerve cells, and converting the analog neurosignals into digital signals; and a signal acquisition unit electrically connected to the AD converter and acquiring the digital signals from the AD converter.

According to embodiments of the present disclosure, the substrate may include a first substrate combined with one end of the severed nerve; a second substrate combined with other end of the severed nerve; and a connecting portion formed as a flexible printed circuit board (FPCB) made of a flexible material, connecting the first and second substrates to each other, and transferring the neurosignal between the first and second substrates.

According to embodiments of the present disclosure, the AD converter may be located between the first substrate and the second substrate to be in contact with the first and second substrates.

According to embodiments of the present disclosure, the first substrate and the second substrate may be disposed to be spaced apart from each other, and the AD converter may be disposed between the first substrate and the second substrate so as to be adjacent to at least one of the first and second substrates.

According to embodiments of the present disclosure, the substrate may be formed as an FPCB made of a flexible material, be bent 180 degrees in a middle, and come into contact with the cut surfaces of the severed nerve on both sides thereof.

According to embodiments of the present disclosure, each of the channels may have a shape of a cavity arranged in the substrate.

According to embodiments of the present disclosure, each of the channels may include a microelectrode layer made of gold (Au) material formed along an inner wall of each channel, and the nerve cell may be combined with the microelectrode layer in the channel by electrical stimulation.

Another aspect is a multi-channel micro peripheral nerve sensor for measuring a neurosignal that includes first and second substrates disposed to be spaced apart from each other, respectively combined with cut surfaces of a severed nerve, and including a plurality of channels into which nerve cells are inserted; an analog-digital (AD) converter embedded in one of the first and second substrates, electrically connected to the plurality of channels, receiving analog neurosignals from the nerve cells, and converting the analog neurosignals into digital signals; a connecting portion formed as a flexible printed circuit board (FPCB) made of a flexible material, connecting the first and second substrates to each other, and transferring the neurosignal between the first and second substrates; and a signal acquisition unit electrically connected to the AD converter and acquiring the digital signals from the AD converter.

The multi-channel micro peripheral nerve sensor according to the present disclosure can reduce the noise of the acquired neurosignal because the AD converter is directly provided in or on the substrate combined with the nerve.

In addition, the multi-channel micro peripheral nerve sensor according to the present disclosure can allow easy interpretation of motion intention for motion control or prosthetic arm or leg control in response to muscle stimulation.

Also, the multi-channel micro peripheral nerve sensor according to the present disclosure can allow easy interpretation of motion intention for natural control of a wearable robot for strengthening or protecting muscle strength such as exoskeleton robot or a soft robot.

DETAILED DESCRIPTION

Figure 1:
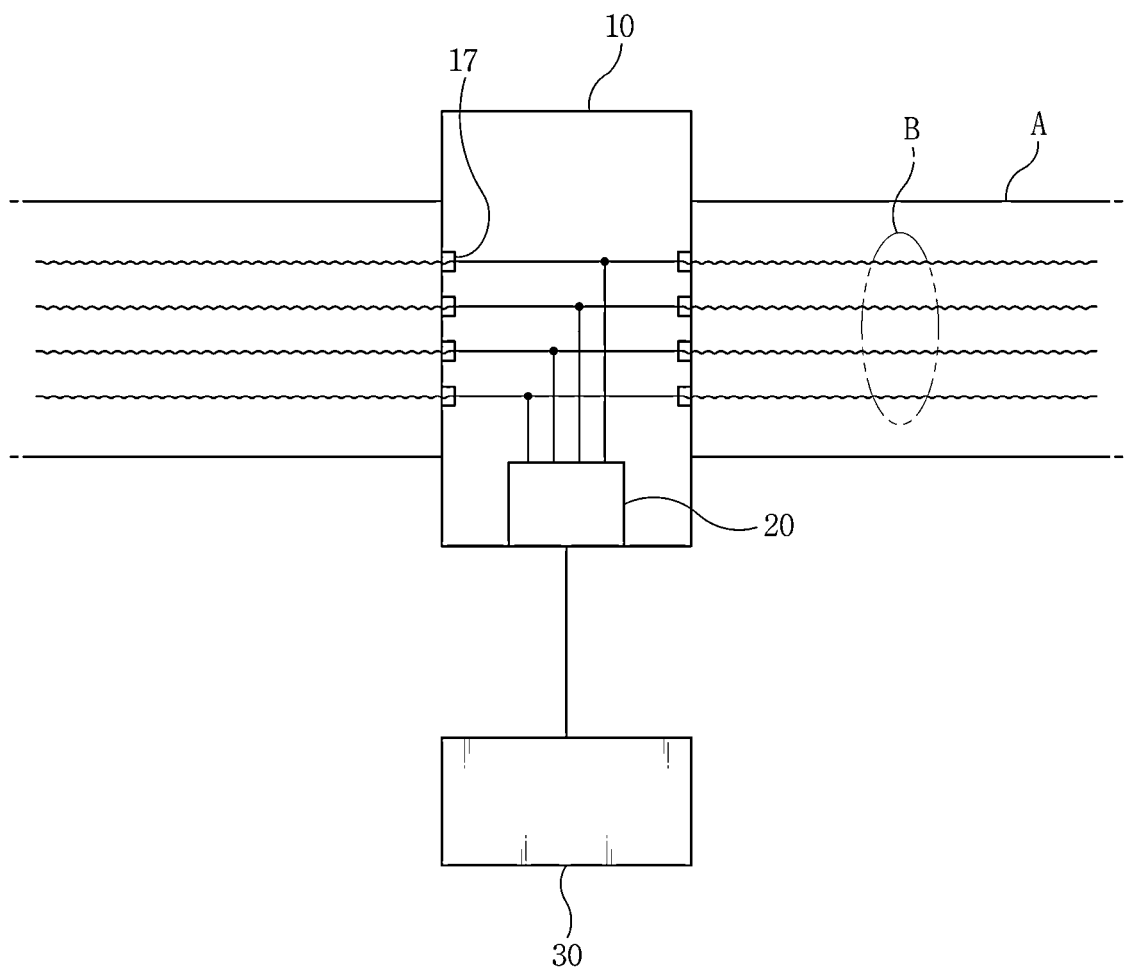
FIG. 1 is a diagram showing a multi-channel micro peripheral nerve sensor for measuring a neurosignal according to the present disclosure.

A peripheral nerve sensor for long-term peripheral motor neurosignal measurement is needed for self-rehabilitation and restoration of body functions for patients whose muscles are paralyzed or weakened due to motor nervous system abnormalities or whose body parts have been amputated due to accidents.

A conventional peripheral nerve sensor is composed of a substrate, an AD converter, and a signal acquisition unit. The substrate is in contact with both ends of the severed nerve and includes a plurality of channels. The AD converter is electrically connected to the substrate and located outside the nerve, and converts neurosignals emitted from a plurality of nerve cells into digital signals. The signal acquisition unit acquires the digital signals of the AD converter.

However, in the conventional peripheral nerve sensor, because the AD converter is located outside the nerve, a lot of noise is contained in the neurosignals transmitted to the AD converter.

Now, embodiments of the present disclosure will be described in detail with reference to the accompanying drawings.

However, in the following description and the accompanying drawings, well known techniques may not be described or illustrated in detail to avoid obscuring the subject matter of the present disclosure. Through the drawings, the same or similar reference numerals denote corresponding features consistently.

The terms and words used in the following description, drawings and claims are not limited to the bibliographical meanings thereof and are merely used by the inventor to enable a clear and consistent understanding of the disclosure. Thus, it will be apparent to those skilled in the art that the following description about various embodiments of the present disclosure is provided for illustration purpose only and not for the purpose of limiting the disclosure as defined by the appended claims and their equivalents.

Figure 2:
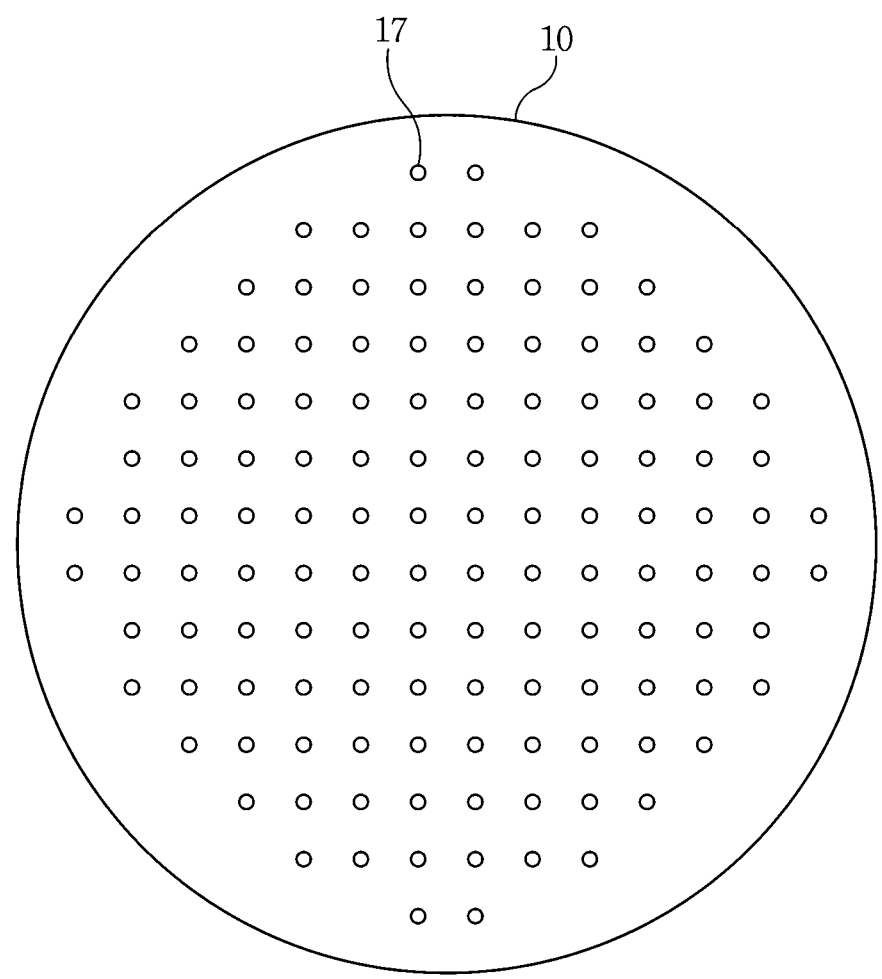
FIG. 2 is a diagram showing a substrate according to the present disclosure.

FIG. 1 is a diagram showing a multi-channel micro peripheral nerve sensor for measuring a neurosignal according to the present disclosure. FIG. 2 is a diagram showing a substrate according to the present disclosure.

Referring to FIG. 1, the multi-channel micro peripheral nerve sensor for measuring a neurosignal according to the present disclosure includes a substrate 10, an AD converter 20, and a signal acquisition unit (or a signal acquisition processor) 30. The substrate 10 is combined with each cut surface of a severed nerve A and includes channels 17 into which nerve cells B are inserted. The AD converter 20 is combined with the substrate 10, is electrically connected to the channels 17, receives analog neurosignals from the nerve cells B, and converts the analog neurosignals into digital signals. The signal acquisition unit 30 is electrically connected to the AD converter 20 and acquires the digital signals from the AD converter 20.

A peripheral nerve (hereinafter referred to as 'nerve A') sends a signal generated in the brain down to other parts of the body, or sends a sensory signal felt at the extremities of the body up to the brain. The nerve A is a bundle of axons extending from the nucleus of the nerve cells B and has a cylindrical structure like a bundle of wires.

The substrate 10 may form a certain shape with a predetermined strength and may be made of any bio-friendly material. The substrate 10 is combined with each cut surface of the severed nerve A. The nerve A includes a plurality of nerve cells B. The nerve cells B are also called axons or nerve fibers.

Referring to FIG. 2, the plurality of channels 17 are arranged in the substrate 10. Each channel 17 may be in the form of a cavity extending from one surface of the substrate 10 to a predetermined length to have a space therein. Alternatively, each channel 17 may be in the form of a cavity extending from one surface of the substrate 10 to the other surface to have a space therein.

For example, the substrate 10 may have a diameter of 3 mm and a distance between channels of 200 μm.

Referring back to FIG. 1, both surfaces of the substrate 10 are in contact with both cut surfaces of the nerve A, respectively. As described above, one end of the nerve cell B is in contact with each of the plurality of channels 17 included on each surface of the substrate 10.

When the nerve A and nerve cell B are severed, the connection of the neurosignal is cut off between both severed sides of the nerve cell B. In this case, the function of the nerve cell B is deteriorated, and when a long time passes, the terminal nerve cell B eventually dies.

Therefore, it is necessary to electrically connect the severed sides of the nerve cell B to transmit and receive a neurosignal therebetween. The plurality of channels 17 are provided in the form of cavities on both surfaces of the substrate 10 in contact with the severed nerve A.

As shown in FIG. 1, the plurality of channels 17 arranged on one of both surfaces of the substrate 10 are electrically connected to the corresponding plurality of channels 17 arranged on the other surface of the substrate 10. Electrical connection between the channels 17 may be made by a connecting portion 15 to be described later. Each channel 17 is electrically connected between both surfaces of the substrate 10 to transmit and receive a neurosignal of the severed nerve cell B.

Each channel 17 may be a microelectrode made of gold (Au). Alternatively, a plurality of microelectrode layers made of Au may be formed on the inner wall of each channel 17. The damaged and severed nerve cell B may be fixed to each channel 17 or regenerated toward the inside of each channel 17 by electrical stimulation by the microelectrode or the microelectrode layers. Therefore, the nerve cell B is fixed to the inner wall of the channel 17 and one surface of the substrate 10.

The plurality of severed nerve cells B included in the severed nerve A are reproduced and fixed to the plurality of channels 17 formed on the substrate 10. The nerve cells B can be inserted into the channels 17 by electrical stimulation. Regeneration of the nerve cells B by electrical stimulation is a method known to those skilled in the art, and thus a detailed description thereof will be omitted.

Referring back to FIG. 1, the AD converter 20 is electrically connected to the plurality of channels 17 included in the substrate 10. The nerve cells B fixed to the plurality of channels 17 transmit unique neurosignals, respectively. The AD converter 20 receives the analog signals of the nerve cells B and converts them into digital signals. The AD converter 20 is combined with the substrate 10 by being embedded inside the substrate 10 or mounted on the outside of the substrate 10.

Conventionally, the AD converter 20 which is far from the substrate 10 causes a lot of noise in the acquired neurosignal. In contrast, the AD converter 20 according to the present disclosure is located within the substrate 10 or mounted directly on the substrate 10, so it is possible to reduce the noise of the acquired neurosignal.

Meanwhile, the multi-channel micro peripheral nerve sensor for measuring neurosignals according to the present disclosure may further include a signal amplifier (not shown) for amplifying neurosignals received from nerve cells B. The signal amplifier may be electrically connected between the substrate 10 and the AD converter 20, especially, between the channel 17 included in the substrate 10 and the AD converter 20. Because the neurosignal transmitted by the nerve cell B may be weak, the signal amplifier is capable of amplifying the neurosignal received from the nerve cell B.

The signal acquisition unit 30 is electrically connected to the AD converter 20 and acquires neurosignals in the form of digital signals from the AD converter 20. The neurosignals acquired by the signal acquisition unit 30 can be used to interpret motion intention for motion control or prosthetic arm or leg control in response to muscle stimulation or to interpret motion intention for natural control of a wearable robot for strengthening or protecting muscle strength such as exoskeleton robot or a soft robot.

Figure 3:
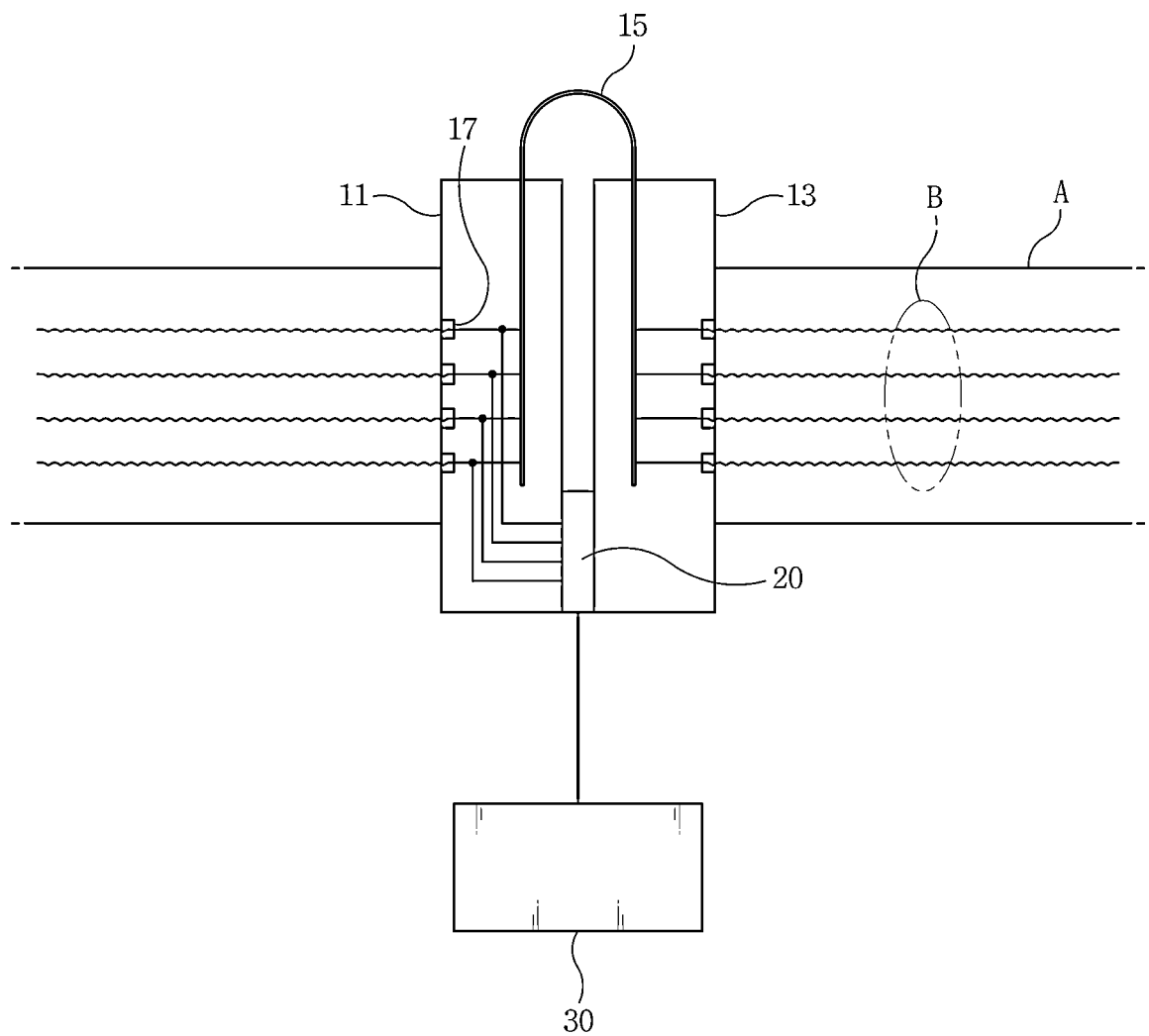
FIGS. 3 to 5 are diagrams showing substrates of different forms according to various embodiments of the present disclosure.
Figure 4:
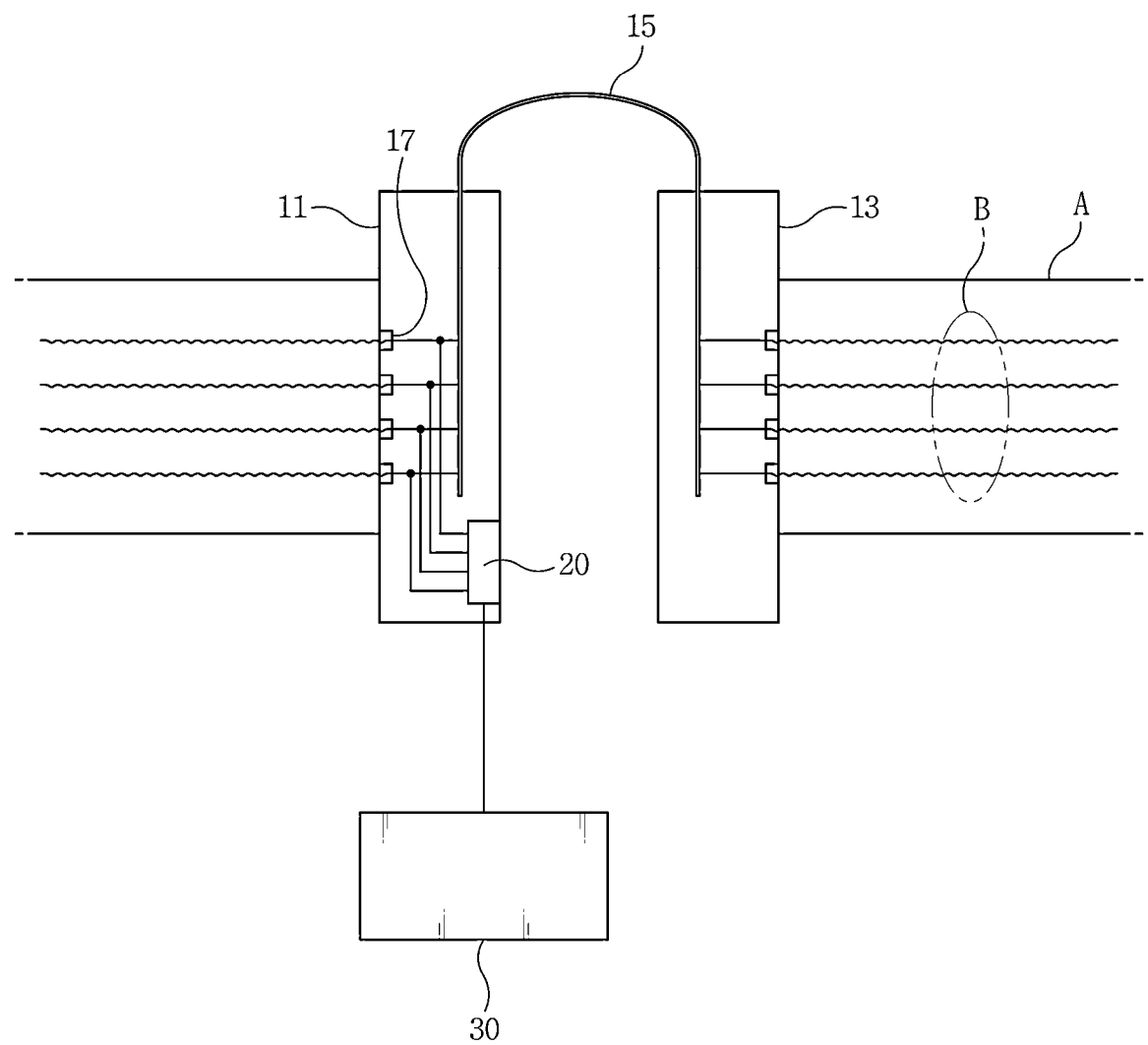
Figure 5:
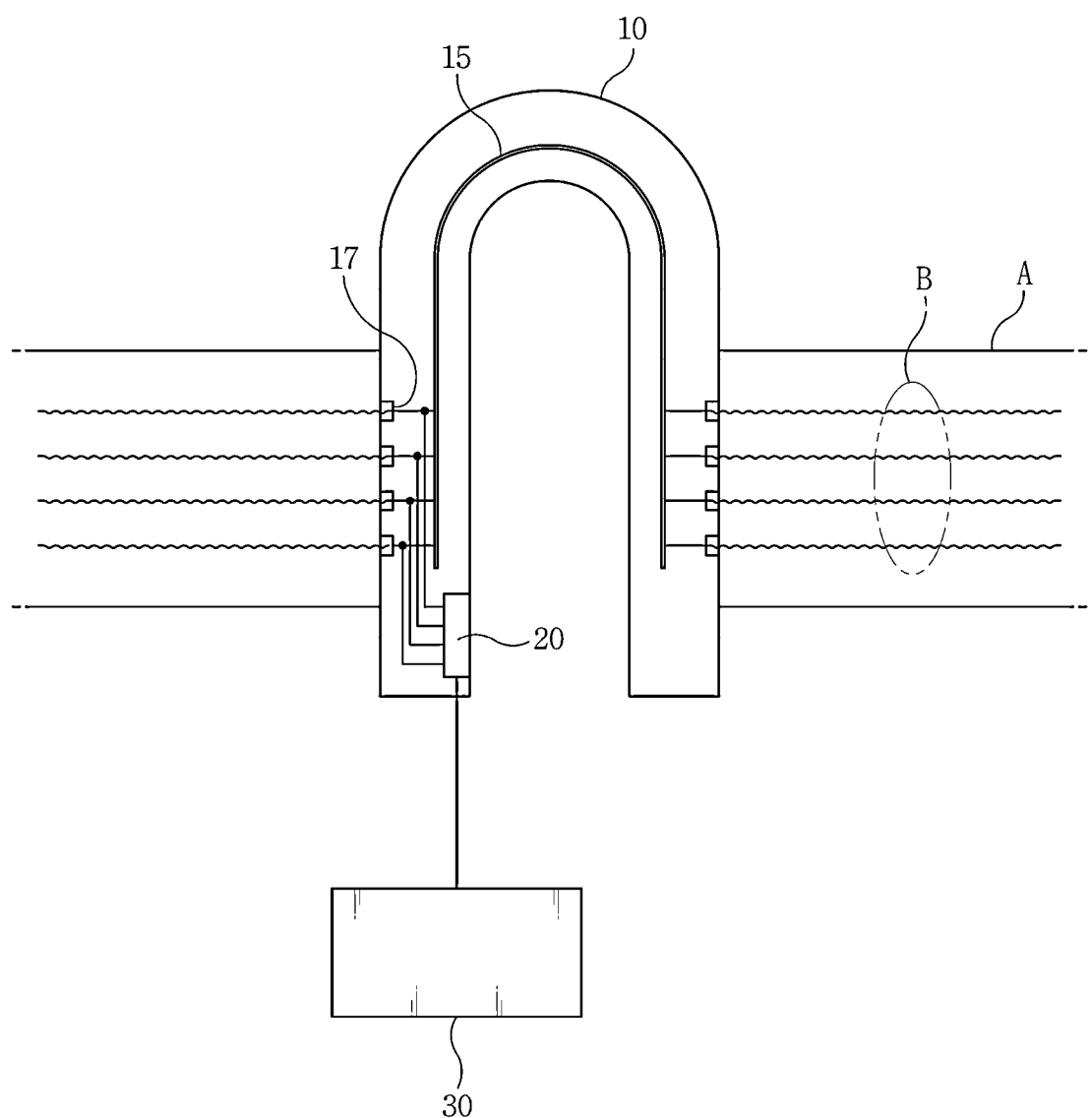

FIGS. 3 to 5 are diagrams showing substrates of different forms according to various embodiments of the present disclosure.

First Embodiment

FIG. 3 is a diagram showing a multi-channel micro peripheral nerve sensor for measuring a neurosignal according to the first embodiment of the present disclosure.

Referring to FIG. 3, the substrate 10 according to the first embodiment includes a first substrate 11 and a second substrate 13, and further includes a connecting portion 15 connecting the first and second substrates 11 and 13.

The first substrate 11 and the second substrate 13 are combined with one end and the other end of the severed nerve A, respectively. The first substrate 11 and the second substrate 13 are electrically connected to each other by the connecting portion 15 formed as a flexible printed circuit board (FPCB) made of a flexible material. The above-described plurality of channels 17 are arranged on each surface of the first and second substrates 11 and 13 facing the cut surface of the severed nerve A.

As described above, the nerve cells B are fixed to the plurality of channels 17. The neurosignals transmitted by the nerve cells B are transferred between the first substrate 11 and the second substrate 13 through the connecting portion 15. As described above, it is necessary to connect the neurosignal between the severed sides of the nerve cell B. The connecting portion 15 electrically connects the severed sides of the nerve cell B to transmit and receive the neurosignal.

As shown in FIG. 3, the AD converter 20 according to the first embodiment is located between the first substrate 11 and the second substrate 13 to be in contact with the first and second substrates 11 and 13. The first substrate 11 and the second substrate 13 are fixed via the AD converter 20 interposed therebetween. The AD converter 20 is electrically connected to each channel 17 in order to receive the neurosignal from the nerve cell B fixed to each channel 17. The AD converter 20 is electrically connected to the signal acquisition unit 30. The signal acquisition unit 30 may be located outside the nerve A. As described above, the signal acquisition unit 30 acquires the digital neural signal from the AD converter 20.

Second Embodiment

FIG. 4 is a diagram showing a multi-channel micro peripheral nerve sensor for measuring a neurosignal according to the second embodiment of the present disclosure.

Referring to FIG. 4, the substrate 10 according to the second embodiment includes the first substrate 11 and the second substrate 13, which are disposed to be spaced apart from each other. The first substrate 11 and the second substrate 13 are spaced apart so as to have a predetermined space. As shown in FIG. 4, the AD converter 20 may be embedded inside the first substrate 11.

Alternatively, the AD converter 20 may be positioned in the space between the first substrate 11 and the second substrate 13. In this case, the AD converter 20 may be in contact with any one of the first substrate 11 and the second substrate 13. Alternatively, instead of the single AD converter 20, two AD converters 20 may be used to be in contact with the first and second substrates 11 and 13, respectively.

The neurosignal is transmitted from one side of the nerve cell B to the other side, and vice versa. The AD converter 20 is preferably connected to the substrate 11 or 13 where the neurosignal comes. That is, the AD converter 20 is preferably combined with the substrate 11 or 13 disposed in the direction to be measured. In order to measure all the neurosignals coming from both sides of the nerve A, the AD converter 20 may be combined with each of the first and second substrates 11 and 13. Alternatively, it is also possible that the AD converter 20 is electrically connected to the first substrate 11 and the second substrate 13 at the same time.

As in the first embodiment, the first substrate 11 and the second substrate 13 are electrically connected to each other by the connecting portion 15 formed as an FPCB made of a flexible material. The above-described plurality of channels 17 are arranged on each surface of the first and second substrates 11 and 13 facing the cut surface of the severed nerve A.

As described above, the nerve cells B are fixed to the plurality of channels 17. The neurosignals transmitted by the nerve cells B are transferred between the first substrate 11 and the second substrate 13 through the connecting portion 15. As described above, it is necessary to connect the neurosignal between the severed sides of the nerve cell B. The connecting portion 15 electrically connects the severed sides of the nerve cell B to transmit and receive the neurosignal.

The channels 17 arranged on each of the first and second substrates 11 and 13 and the nerve cells B fixed to the channels 17 are the same as those described above, so the description thereof will be omitted. Meanwhile, as in the first embodiment, in the second embodiment, the signal amplifier for amplifying the neurosignal may be further included to be electrically connected between each channel 17 and the AD converter 20, and the signal acquisition unit 30 for acquiring the digital signal received from the AD converter 20 may be further included.

The multi-channel micro peripheral nerve sensor for measuring a neurosignal according to the second embodiment is as follows.

The multi-channel micro peripheral nerve sensor includes the first substrate 11 and the second substrate 13, which are spaced apart from each other, are in contact with the corresponding cut surfaces of the severed nerve A, and have the plurality of channels 17 into which the nerve cells B are inserted. The AD converter is embedded in either the first substrate 11 or the second substrate 13. The AD converter 20 is electrically connected to the plurality of channels 17, receives analog neurosignals from the nerve cells B, and converts them into digital signals. The first substrate 11 and the second substrate 13 are connected by the connecting portion 15 formed as an FPCB made of a flexible material. The connecting portion 15 transmits the neurosignal transmitted by the nerve cell B on one side to the nerve cell B on the other side. The signal acquisition unit 30 is electrically connected to the AD converter 20 and acquires the digital signal from the AD converter 20. The signal acquisition unit 30 may be located outside the nerve A.

Third Embodiment

FIG. 5 is a diagram showing a multi-channel micro peripheral nerve sensor for measuring a neurosignal according to the third embodiment of the present disclosure.

Referring to FIG. 5, the substrate 10 according to the third embodiment is formed as an FPCB made of a flexible material, is bent 180 degrees in the middle, and comes into contact with the cut surfaces of the severed nerve A on both sides thereof. As in the first and second embodiments, the plurality of channels 17 are arranged at positions of the substrate 10 where are in contact with each cut surface of the severed nerve A. The nerve cells B are fixed to the respective channels 17, which are electrically connected to the AD converter 20.

The AD converter 20 may be embedded in the substrate 10 at a location close to the nerve A on one side. Alternatively, the AD converter 20 may be positioned to be in contact with the inner surface of the bent substrate 10. The signal amplifier for amplifying the neurosignal may be further included between the channels 17 and the AD converter 20.

In addition, the signal acquisition unit 30 electrically connected to the AD converter 20 is further included. As described above, the signal acquisition unit 30 acquires the neurosignals in the form of digital signals from the AD converter 20.

According to the third embodiment, the substrate 10 may contain therein the connecting portion 15 for transmitting the neurosignal between the severed nerve cells B. As described above, the connecting portion 15 may be made of a flexible material.

While the present disclosure has been particularly shown and described with reference to an exemplary embodiment thereof, it will be understood by those skilled in the art that various changes in form and details may be made therein without departing from the scope of the present disclosure as defined by the appended claims.

What is claimed is:

1. A multi-channel micro peripheral nerve sensor for measuring a neurosignal, comprising:
   one or more substrates configured to couple with a first cut end and a second cut end of a severed nerve and including first channels configured to receive first nerve cells of the first cut end and second channels configured to receive second nerve cells of the second cut end;
   a connecting portion connecting the first channels and the second channels and configured to allow analog neurosignals to be transferred from the first nerve cells to the second nerve cells therethrough, the connecting portion being in direct physical contact with at least one of the one or more substrates;
   an analog-digital (AD) converter being in direct physical contact with at least one of the one or more substrates, electrically connected to the first channels, and configured to receive the analog neurosignals from the first nerve cells and convert the analog neurosignals into digital signals;
   a signal acquisition processor electrically connected to the AD converter and configured to acquire the digital signals from the AD converter; and
   wherein the one or more substrates include:
   a first substrate configured to couple with the first cut end of the severed nerve;
   a second substrate separated from the first substrate and is configured to couple with the second cut end of the severed nerve, and
   wherein the connecting portion has a reverse U shape including a linear portion and a curved portion, wherein at least part of the linear portion is embedded in each of the first and second substrates.

2. The multi-channel micro peripheral nerve sensor of claim 1,
   wherein the curved portion of the connecting portion is one of: embedded in each of the first and second substrates, or disposed outside the first and second substrates,
   wherein the connecting portion is formed as a flexible printed circuit board (FPCB) made of a flexible material, configured to connect the first and second substrates to each other, and transfer the analog neurosignals between the first and second substrates,
   wherein the AD converter is either disposed between the first and second substrates, or embedded in one of the first substrate or the second substrate.

3. The multi-channel micro peripheral nerve sensor of claim 1, wherein each of the one or more substrates is formed as an FPCB made of a flexible material, is bent 180 degrees in a middle, and configured to come into contact with the first and second ends of the severed nerve.

4. The multi-channel micro peripheral nerve sensor of claim 1, wherein each channel of the first and second channels has a shape of a cavity arranged in the one or more substrates.

5. The multi-channel micro peripheral nerve sensor of claim 1, wherein each channel of the first and second channels includes a microelectrode layer made of gold (Au) material formed along an inner wall of each channel, and one nerve cell of the first and second nerve cells is coupled to the microelectrode layer in a corresponding channel of the first and second channels by electrical stimulation.

6. The multi-channel micro peripheral nerve sensor of claim 1, further comprising a signal amplifier connected between the first channels and the AD converter.

7. A multi-channel micro peripheral nerve sensor for measuring a neurosignal, comprising:
   a first substrate configured to couple with a first cut end a severed nerve and comprising first channels configured to receive first nerve cells of the first cut end;
   a second substrate disposed to be spaced apart from the first substrate, configured to couple with a second cut end of the severed nerve, and including second channels configured to receive second nerve cells of the second cut end;
   a connecting portion formed as a flexible printed circuit board (FPCB) made of a flexible material, and configured to connect the first and second substrates to each other configured to allow analog neurosignals are transferred from the first nerve cells to the second nerve cells therethrough, the connecting portion being in direct physical contact with both of the first and second substrates;
   an analog-digital (AD) converter embedded in the first substrate, electrically connected to the first channels, and configured to receive the analog neurosignals transferred from the first nerve cells and convert the analog neurosignals into digital signals; and
   a signal acquisition unit electrically connected to the AD converter and configured to acquire the digital signals from the AD converter, and
   wherein the connecting portion has a reverse U shape including a linear portion and a curved portion, wherein at least part of the linear portion is embedded in each of the first and second substrates, wherein the curved portion of the connecting portion is embedded in each of the first and second substrates, or disposed outside the first and second substrates.

8. The multi-channel micro peripheral nerve sensor of claim 7, further comprising an additional AD converter combined with the second substrate and connected to the second channels.

* * * * *